(12) United States Patent
Kunieda et al.

(10) Patent No.: US 8,193,137 B2
(45) Date of Patent: *Jun. 5, 2012

(54) THICKENING COMPOSITION

(75) Inventors: Hironobu Kunieda, Yokohama (JP); Akemi Kunieda, legal representative, Yokohama (JP); Kazuhiko Tobita, Kawasaki (JP); Koichiro Sagawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/037,768

(22) Filed: Mar. 1, 2011

(65) Prior Publication Data

US 2011/0152148 A1    Jun. 23, 2011

Related U.S. Application Data

(63) Continuation of application No. 12/781,504, filed on May 17, 2010, now abandoned, which is a continuation of application No. 11/501,741, filed on Aug. 10, 2006, now abandoned, which is a continuation of application No. PCT/JP2005/002513, filed on Feb. 10, 2005.

(30) Foreign Application Priority Data

Feb. 13, 2004   (JP) ................................ 2004-037365
Sep. 17, 2004   (JP) ................................ 2004-271394

(51) Int. Cl.
   *C11D 1/88*    (2006.01)
   *C11D 3/26*    (2006.01)
   *C11D 3/20*    (2006.01)
   *C11D 3/43*    (2006.01)

(52) U.S. Cl. ........ 510/126; 510/123; 510/130; 510/136; 510/137; 510/138; 510/477; 510/488; 510/501; 510/505; 510/506; 424/70.19; 424/70.21

(58) Field of Classification Search .................. 510/123, 510/126, 130, 136, 137, 138, 477, 488, 501, 510/505, 506; 424/70.19, 70.21
See application file for complete search history.

(56) References Cited

U.S. PATENT DOCUMENTS

| | | | |
|---|---|---|---|
| 4,272,515 | A | 6/1981 | Hofman et al. |
| 5,616,552 | A | 4/1997 | Yoshihara et al. |
| 5,639,450 | A | 6/1997 | Oldenhove de Guertechin |
| 7,947,260 | B2 * | 5/2011 | Tobita .................. 424/70.22 |
| 2003/0083210 | A1 | 5/2003 | Goldberg et al. |
| 2007/0213244 | A1 | 9/2007 | Tobita et al. |

FOREIGN PATENT DOCUMENTS

| | | |
|---|---|---|
| DE | 299 10 159 U 1 | 11/2000 |
| DE | 100 57 768 A1 | 5/2002 |
| DE | 102 04 099 A1 | 8/2003 |
| EP | 0 303 187 A2 | 2/1989 |
| EP | 0 374 415 A2 | 6/1990 |
| EP | 0 569 028 A2 | 11/1993 |
| EP | 1 180 363 A2 | 2/2002 |
| GB | 2 026 532 A | 2/1980 |
| JP | 58-27636 | 2/1983 |
| JP | 60-193529 | 10/1985 |
| JP | 06-057290 | 3/1994 |
| JP | 06-158089 | 6/1994 |
| JP | 06-264090 | 9/1994 |
| JP | 07-011288 | 1/1995 |
| JP | 09-301846 | 11/1997 |
| JP | 2001-220597 | 8/2001 |
| JP | 2001-247448 | 9/2001 |
| JP | 2002-53896 | 2/2002 |
| JP | 2003-055690 | 2/2003 |
| JP | 2003-089614 | 3/2003 |
| JP | 2003-160797 | 6/2003 |
| JP | 3922299 | 5/2007 |
| WO | WO 99/06518 | 2/1999 |
| WO | WO 02/05758 A2 | 1/2002 |
| WO | WO 03/013459 A2 | 2/2003 |
| WO | WO 2005/048971 A1 | 6/2005 |

OTHER PUBLICATIONS

Y. Koda et al, Organic Conception Diagram—Basic and Application, Sankyo Publishing Co., Ltd., 1984, pp. 12-13.
Formulation Design by The Organic Conceptional Diagram, Nihon Emulsion Co., Ltd., 1997, p. 6.
Formulation Design with Organic Conception Diagram, Nihon Emulsion Co., Ltd., 1998, pp. 1-55.
"Viscosity Increasing Agents-Nonaqueous (PASSAGE)", International Cosmetic Ingredient Dictionary and Handbook, Tenth Edition, XP007911561, Jan. 1, 2004, pp. 2294-2296 with an additional page.

* cited by examiner

*Primary Examiner* — Gregory Delcotto
(74) *Attorney, Agent, or Firm* — Oblon, Spivak, McClelland, Maier & Neustadt, L.L.P.

(57) ABSTRACT

The present invention provides a thickening composition simultaneously exhibiting suitable thickening performance and superior usability, which contains N-long-chain acyl acidic amino acid and/or a salt thereof, an amphipathic substance, an inorganic salt, and water as essential components, and has a viscosity of not less than 200 mPa·s. By the addition of the thickening composition, moreover, cleansing compositions and cosmetic compositions for skin, hair and the like, which maintain thickening performance and usability, while containing N-long-chain acyl acidic amino acid and/or a salt thereof are provided.

30 Claims, No Drawings

THICKENING COMPOSITION

TECHNICAL FIELD

The present invention relates to thickening compositions containing four components of N-long-chain acyl acidic amino acid and/or a salt thereof, an amphipathic substance, an inorganic salt and water, which simultaneously show suitable thickening performance and superior usability, and cleansing compositions and cosmetic compositions containing the same.

BACKGROUND ART

N-long-chain acyl acidic amino acid and/or a salt thereof have long been known to be useful as less irritant materials as compared to conventionally-used skin or hair cleansing compositions containing an anion surfactant such as alkylsulfate, alkylsulfonate and the like as a main component.

However, addition of N-long chain acyl glutamic acid and/or a salt thereof to skin and hair cleansing compositions containing alkylsulfate, alkylsulfonate, polyoxyethylene alkylether sulfate and the like as a main agent for the purpose of reducing the irritation problematically decreases the viscosity.

To solve this problem, attempts have been made to thicken N-long-chain acyl acidic amino acid-containing cleansing agents by the addition of an ester or ether polymer thickener having a polyoxyethylene chain (JP-A-6-158089), addition of a polysaccharide thickener (JP-A-6-264090) and addition of a cellulose natural polymer derivative (JP-A-2003-55690). However, addition of a sufficient amount of a polymer thickener to ensure viscosity has resulted in new problems relating to the sense of use, such as poor foaming, sliminess during rinsing, which is characteristic of polymers, and the like.

In an effort to thicken N-long-chain acyl acidic amino acid-containing cleansing compositions, moreover, addition of colloidal silicate to an aqueous solution of N-long-chain acyl acidic amino acid salt has been known, though a sufficient viscosity as a liquid cleansing composition cannot be achieved (JP-A-7-11288).

On the other hand, as gel compositions containing a N-long-chain acyl acidic amino acid and/or a salt thereof, a gel composition having thixotropy (JP-A-6-057290), and an aqueous thickening gel composition and a liquid oil-in-water emulsion composition (JP-A-9-301846) have been reported. They are used as base materials for the production of skin external agents such as cosmetic serum, cream and the like, which contain N-long-chain acyl acidic amino acid and/or a salt thereof. However, since these aqueous thickening gel compositions and liquid oil-in-water emulsion compositions do not have a foaming power or a cleaning power, a sufficient function as a skin and hair cleansing composition has not been achieved.

Thus, a thickening composition containing n-long-chain acyl acidic amino acid and/or a salt thereof, which shows suitable thickening performance without impairing the foamability and sense of use of n-long-chain acyl acidic amino acid and/or a salt thereof has been strongly desired.

DISCLOSURE OF THE INVENTION

The present inventors have conducted intensive studies in an attempt to solve the aforementioned problems and found that a thickening composition simultaneously exhibiting suitable thickening performance and superior usability can be obtained by the use of N-long-chain acyl acidic amino acid and/or a salt thereof, an amphipathic substance, an inorganic salt and water as essential components, and that the use of the thickening composition affords a cleansing agent and a cosmetic composition containing N-long-chain acyl acidic amino acid and/or a salt thereof, which satisfy thickening performance and the sense of use.

Accordingly, the present invention comprises the following embodiments.

[1] A thickening composition comprising four components of (A) N-long-chain acyl acidic amino acid and/or a salt thereof, (B) an amphipathic substance, (C) an inorganic salt and (D) water as essential components, which shows a viscosity of not less than 200 mPa·s.

[2] The thickening composition of [1], wherein the amphipathic substance of component (B) shows an organic value and an inorganic value satisfying the following formula [1]:

$$(\text{inorganic value}) \leq -5 \times (\text{organic value}) + 2500 \quad [1]$$

[3] The thickening composition of [1] or [2], wherein the weight ratio of component (A):component (B) is 90:10-30:70, the weight ratio of component (A):component (C) is 99.5:0.5-50:50 and the weight ratio of the total weight of component (A), component (B) and component (C):component (D) is 2:98-70:30.

[4] The thickening composition of any of [1] to [3], wherein the amino acid of component (A) is glutamic acid.

[5] The thickening composition of any of [1] to [4], wherein the acyl group of component (A) derives from one or more kinds selected from the group consisting of caprylic acid, capric acid, lauric acid, myristic acid, stearic acid, palmitic acid, oleic acid, linoleic acid, behenic acid, coconut fatty acid, palm fatty acid and hydrogenated beef tallow fatty acid.

[6] The thickening composition of any of [1] to [5], wherein the component (B) is one or more kinds selected from glyceryl monofatty acid, propyleneglycol monofatty acid, butyleneglycol monofatty acid, diethyleneglycol monofatty acid, monofatty acid N-methylethanolamide, lauryl glycol hydroxypropylether and polyoxypropylene(1)coconut fatty acid monoisopropanolamide.

[7] The thickening composition of any of [1] to [6], wherein the component (B) is glyceryl monofatty acid having not less than 8 and not more than 18 carbon atoms.

[8] The thickening composition of any of [1] to [7], wherein the component (C) is an alkaline earth metal inorganic salt.

[9] The thickening composition of any of [1] to [8], further comprising (E) polyhydric alcohol.

[10] The thickening composition of any of [1] to [9], further comprising (F) chelating agent.

[11] A cleansing composition comprising a thickening composition of any one of [1] to [10].

[12] A cosmetic composition comprising a thickening composition of any one of [1] to [10].

DETAILED DESCRIPTION OF THE INVENTION

N-long-chain acyl acidic amino acid and/or a salt thereof to be used as component (A) in the present invention may be those obtained by known methods. For example, Schotten-Baumann reaction of acidic amino acid and fatty acid halide is widely known.

As the acidic amino acid for component (A), glutamic acid, aspartic acid and the like can be used. These amino acids may be any of an L form, a D form and a DL form, or may be a mixture of two or more kinds selected from these. Since stability and usability of the material after acylation are superior, glutamic acid is preferable.

As the acyl group of component (A), a straight chain or branched chain acyl group derived from saturated or unsaturated fatty acids having 8 to 22 carbon atoms can be used. As fatty acid, for example, caprylic acid, capric acid, lauric acid, myristic acid, stearic acid, isostearic acid, palmitic acid, oleic acid, linoleic acid, behenic acid, coconut fatty acid, palm fatty acid, hydrogenated beef tallow fatty acid, and the like can be mentioned. One kind of these may be used, or two or more kinds selected from the above-mentioned group may be used in a mixture. Particularly, coconut fatty acid, lauric acid and myristic acid are preferable, since they are superior in foaming and foam quality.

The salt of component (A) is not particularly limited and, for example, alkali metals such as sodium, potassium and the like, alkaline earth metals such as calcium, magnesium and the like, inorganic salts such as aluminum, zinc and the like, organic amines such as ammonia, monoethanolamine, diethanolamine, triethanolamine and the like, and organic salts such as basic amino acids (e.g., arginine, lysine and the like) and the like can be mentioned. One kind of these may be used, or two or more kinds selected from the above-mentioned group may be used in a mixture. Alkali metal salts, organic amine salts and basic amino acids are preferable, and sodium, potassium, triethanolamine and arginine are particularly preferable, since they are easily available and superior in handling property and the like.

The amphipathic substance to be used as component (B) in the present invention is not particularly limited structurally as long as it shows surface activity, forms an aggregate with component (A), N-long-chain acyl acidic amino acid salt, based on the balance between hydrophilicity and hydrophobicity, and provides a thickening effect.

For the balance between hydrophilicity and hydrophobicity, those having an organic value and an inorganic value satisfying the range defined by the following relational formula 1 are selected.

(inorganic value)≦−5×(organic value)+2500    [1]

When the inorganic value exceeds −5×(organic value)+2500, the balance necessary for forming an aggregate with component (A), N-long-chain acyl acidic amino acid salt, is disturbed and the thickening effect becomes low. The inorganic value and organic value are calculated from Organic Conception Diagram—Basic and Application (1984) (Yoshio Koda et al., Sankyo Publishing Co., Ltd.) or Emulsion Formulation Design with Organic Conception Diagram (1997) (ed. Nihon Emulsion Co., Ltd.). Both the inorganic value and organic value are 0 or positive numbers.

Specifically, glyceryl monofatty acid, glyceryl difatty acid, glyceryl trifatty acid, propyleneglycol monofatty acid, butyleneglycol monofatty acid, diethyleneglycol monofatty acid Monofatty acid N-methylethanolamide, lauryl glycol hydroxypropylether, polyoxypropylene(1)coconut fatty acid monoisopropanolamide and the like can be mentioned. One kind of these may be used, or two or more kinds selected from the above-mentioned group may be used in a mixture. Of them, glyceryl monofatty acid, propyleneglycol monofatty acid, butyleneglycol monofatty acid, diethyleneglycol monofatty acid Monofatty acid N-methylethanolamide, lauryl glycol hydroxypropylether, and polyoxypropylene(1)coconut fatty acid monoisopropanolamide are preferable, since they are particularly low molecule and superior in usability.

As the glyceryl monofatty acid, glyceryl monocaprylate, glyceryl monocaprate, glyceryl monolaurate, glyceryl monomyristate, glyceryl monopalmitate, glyceryl monostearate, glyceryl monoisostearate and the like can be specifically mentioned. One kind of these may be used, or two or more kinds selected from the above-mentioned group may be used in a mixture. Of these, glyceryl monocaprylate, glyceryl monocaprate, glyceryl monolaurate, glyceryl monomyristate are preferable, since an aggregate is easily formed with component (A), N-long-chain acyl acidic amino acid and/or a salt thereof, and component (C), a salt. As the fatty acid, a saturated or unsaturated fatty acid having 8 to 18 carbon atoms can be used, which may contain substituent(s) to the extent that the effect of the invention is not inhibited. When the carbon number is not more than 8, the thickening effect is low, and when it is not less than 18, the solubility is low, thus permitting easy precipitation. It is preferably 8-14, since stable and sustained thickening performance can be maintained, and more preferably 10-12, since foaming performance can be maintained.

As the propyleneglycol monofatty acid, propyleneglycol monocaprylate, propyleneglycol monocaprate, propyleneglycol monolaurate, propyleneglycol monomyristate, propyleneglycol monopalmitate, propyleneglycol monostearate, propyleneglycol monoisostearate and the like can be specifically mentioned. One kind of these may be used, or two or more kinds selected from the above-mentioned group may be used in a mixture. Of these, propyleneglycol monocaprylate, propyleneglycol monocaprate, propyleneglycol monolaurate and propyleneglycol monomyristate are preferable, since an aggregate is easily formed with component (A), N-long-chain acyl acidic amino acid and/or a salt thereof, and component (C), a salt. As the fatty acid, a saturated or unsaturated fatty acid having 8 to 18 carbon atoms can be used, which may contain substituent to the extent that the effect of the invention is not inhibited. When the carbon number is not more than 8, the thickening effect is low, and when it is not less than 18, the solubility is low, thus permitting easy precipitation. It is preferably 8-14, since stable and sustained thickening performance can be maintained, and more preferably 10-12, since foaming performance can be maintained.

As the butyleneglycol monofatty acid, butyleneglycol monocaprylate, butyleneglycol monocaprate, butyleneglycol monolaurate, butyleneglycol monomyristate, butyleneglycol monopalmitate, butyleneglycol monostearate, butyleneglycol monoisostearate and the like can be specifically mentioned. One kind of these may be used, or two or more kinds selected from the above-mentioned group may be used in a mixture. Of these, butyleneglycol monocaprylate, butyleneglycol monocaprate, butyleneglycol monolaurate and butyleneglycol monomyristate are preferable, since an aggregate is easily formed with component (A), N-long-chain acyl acidic amino acid and/or a salt thereof and component (C), a salt. As the fatty acid, a saturated or unsaturated fatty acid having 8 to 18 carbon atoms can be used, which may contain substituent(s) to the extent that the effect of the invention is not inhibited. When the carbon number is not more than 8, the thickening effect is low, and when it is not less than 18, the solubility is low, thus permitting easy precipitation. It is preferably 8-14, since stable and sustained thickening performance can be maintained, and more preferably 10-12, since foaming performance can be maintained.

As the diethyleneglycol monofatty acid, diethyleneglycol monocaprylate, diethyleneglycol monocaprate, diethyleneglycol monolaurate, diethyleneglycol monomyristate, diethyleneglycol monopalmitate, diethyleneglycol monostearate, diethyleneglycol monoisostearate and the like can be specifically mentioned. One kind of these may be used, or two or more kinds selected from the above-mentioned group may be used in a mixture. Of these, diethyleneglycol monocaprylate, diethyleneglycol monocaprate, diethyleneglycol monolaurate and diethyleneglycol monomyristate are preferable, since an aggregate is easily formed with component (A), N-long-chain acyl acidic amino acid and/or a salt thereof and component (C), a salt. As the fatty acid, a saturated or unsaturated fatty acid having 8 to 18 carbon atoms can be used, which may contain substituent(s) to the extent that the effect of the invention is not inhibited. When the carbon number is not more than 8, the thickening effect is low, and when it is not less than 18, the solubility is low, thus permitting easy precipitation. It is preferably 8-14, since stable and sustained thickening performance can be maintained, and more preferably 10-12, since foaming performance can be maintained.

As the monofatty acid N-methylethanolamide, monocapryloyl N-methylethanolamide, monocaproyl N-methylethanolamide, monolauroyl N-methylethanolamide, monomyristoyl N-methylethanolamide, monopalmitoyl N-methylethanolamide, monostearoyl N-methylethanolamide, monoisostearoyl N-methylethanolamide and the like can be specifically mentioned. One kind of these may be used, or two or more kinds selected from the above-mentioned group may be used in a mixture. Of these, monocapryloyl N-methylethanolamide, monocaproyl N-methylethanolamide, monolauroyl N-methylethanolamide, and monomyristoyl N-methylethanolamide are preferable, since an aggregate is easily formed with component (A), N-long-chain acyl acidic amino acid and/or a salt thereof and component (C), a salt. As the fatty acid, a saturated or unsaturated fatty acid having 8 to 18 carbon atoms can be used, which may contain substituent(s) to the extent that the effect of the invention is not inhibited. When the carbon number is not more than 8, the thickening effect is low, and when it is not less than 18, the solubility is low, thus permitting easy precipitation. It is preferably 8-14, since stable and sustained thickening performance can be maintained, and more preferably 10-12, since foaming performance can be maintained.

As the lauryl glycol hydroxypropyl ether, commercially available Viscosafe LPE (manufactured by Kawaken Fine Chemicals Co., Ltd.) can be specifically mentioned.

As the polyoxypropylene(1)coconut fatty acid monoisopropanolamide, commercially available Amizett 1PC (manufactured by Kawaken Fine Chemicals Co., Ltd.) can be specifically mentioned.

The inorganic salt to be used as component (C) in the present invention is not particularly limited and salts with mineral acids such as sulfuric acid, hydrochloric acid, phosphoric acid and the like, salts with carbonic acid, salts with alkali metal and salts with alkaline earth metal can be mentioned. Specifically, sodium chloride, potassium chloride, magnesium chloride, calcium chloride, sodium sulfate, sodium hydrogensulfate, potassium sulfate, potassium hydrogensulfate, magnesium sulfate, calcium sulfate, monobasic sodium phosphate, dibasic sodium phosphate, monobasic potassium phosphate, dibasic potassium phosphate, sodium carbonate, sodium hydrogencarbonate, potassium carbonate, potassium hydrogencarbonate, magnesium carbonate, calcium carbonate and the like can be mentioned. One kind of these may be used, or two or more kinds selected from the above-mentioned group may be used in a mixture. Particularly, alkaline earth metal salt is preferable, calcium salt and magnesium salt are more preferable, and magnesium salt is still more preferable, since the thickening effect is high.

As the counter anion, chloride ion is preferable, since a thickening effect and high transparency can be afforded. As specific compounds, calcium chloride and magnesium chloride are preferable, and magnesium chloride is particularly preferable.

Water to be used as component (D) in the present invention is not particularly limited as long as it has a purity of the level applicable to cleansing agents and cosmetic compositions. Specifically, ion-exchanged water, well water, natural water, groundwater, public water, hard water, soft water and the like can be used. One kind of these may be used, or two or more kinds selected from the above-mentioned group may be used in a mixture. Ion-exchanged water is preferable from the aspects of preservation stability and hygiene of the product of the present invention.

The weight ratio of component (A) and component (B) to be used in the present invention is generally 90:10-30:70. When the component (B) is less than 10, the thickening effect becomes weak, and when component (B) is greater than 70, a problem of easy precipitation occurs. The ratio is preferably 85:15-35:65 since an aggregate of component (A) and component (B) is easily formed and sustainability is afforded. It is more preferably 85:15-50:50, since sufficient foamability and liquid composition can be achieved.

The weight ratio of component (A) and component (C) to be used in the present invention is generally 99.5:0.5-50:50. When component (C) is less than 0.5, the thickening effect is low, and when it is greater than 50, precipitation and the like problematically occur. The weight ratio of 99:1-55:45 is preferable, since a stable and sustained thickening effect can be expected.

The weight ratio of the total weight of component (A), component (B) and component (C) to be used in the present invention and component (D) is generally 2:98-70:30. When the total weight of component (A), component (B) and component (C) is less than 2, the function of the cleansing agent, such as foaming, foam quality and the like, become insufficient and the thickening effect also becomes low, and when it is greater than 70, precipitation and the like occur, thus problematically degrading the usability. The ratio of 2.5:97.5-50:50 is preferable, since usability as a cleansing agent and stable and sustained thickening effect can be afforded.

The weight ratio of component (A) and component (D) in a thickening composition is generally 0.5:99.5-68:32. It is preferably 1:99-46:54, more preferably 5:95-40:60, to achieve usability as a cleansing agent. When component (A) is less than 0.5, sufficient cleansing effect and moist feeling after washing cannot be afforded, and when component (A) is greater than 68, usability is problematically degraded.

The production method of the thickening composition of the present invention includes mixing component (A), component (B) and component (D) at a given ratio, dissolving them by heating at 60-80° C., and adding component (C) to give a uniform solution. Thereafter, the mixture is cooled to room temperature to give a thickening composition.

The thickening composition of the present invention has a viscosity of generally 200 mPa·s-50000 mPa·s. The viscosity can be freely controlled by changing the ratio of components (A), (B), (C) and (D). It is preferably 250 mPa·s-40000 mPa·s, more preferably 300 mPa·s-25000 mPa·s, still more preferable 350 mPa·s-10000 mPa·s, from the aspect of easy use as a cleansing composition.

The thickening composition of the present invention can be added to cosmetic compositions and cleansing compositions. While the component (A) in the entire cosmetic composition and cleansing composition is not particularly limited, its content is generally selected from the range of 0.2-60%. When component (A) is less than 0.2%, the effect as a thickening composition tends to be unremarkable, and when it is greater than 60%, sufficient usability as a cosmetic composition or cleansing composition may be lost. Since a remarkable thickening effect is exhibited, its lower limit is preferably not less than 0.3%, more preferably not less than 0.5%, still more preferably not less than 1%, further preferably not less than 2%, and particularly preferably not less than 3%. Since cosmetic competitions and cleansing compositions with good sense of use can be provided, its upper limit is preferably not more than 55%, more preferably not more than 50%, still more preferably not more than 45%, further preferably not more than 40%, and particularly preferably not more than 35%.

While cosmetic compositions and cleansing compositions containing the thickening composition of the present invention show a good viscosity of generally 200 mPa·s-50000 mPa·s, it is preferably 250 mPa·s-40000 mPa·s, more preferably 300 mPa·s-25000 mPa·s, still more preferably 350 mPa·s-10000 mPa·s, since such cosmetic compositions and cleansing compositions are easy to use.

As the thickening composition of the present invention, the above-mentioned thickening composition of the present invention preferably contains (E) polyhydric alcohol, since a further thickening effect can be exhibited. As the polyhydric alcohol, glycerol, diglycerol, sorbitol, propylene glycol, dipropylene glycol, butylene glycol, polyethylene glycol and the like can be mentioned. Since a superior thickening effect is exhibited, not less than trivalent polyhydric alcohol is preferable, glycerol, diglycerol and sorbitol are more preferable, and sorbitol is particularly preferable.

As the polyhydric alcohol of component (E), one kind or two or more kinds may be used in combination. While its content is not particularly limited, it is preferably 0.2-50 wt %, more preferably 1-20 wt %, relative to the whole composition. When the content of component (E) is less than 0.2 wt %, a sufficient thickening effect cannot be afforded and a moist feeling that should be provided by polyhydric alcohol is not sufficiently obtained. When the content is greater than 50 wt %, foaming and a feeling of the composition are degraded.

As the thickening composition of the present invention, the above-mentioned thickening composition of the present invention preferably contains (F) a chelating agent, since a more superior thickening effect can be exhibited. As the chelating agent, ethylenediamine tetraacetic acid and/or a salt thereof (EDTA), hydroxyethyl ethylenediamine triacetic acid and/or a salt thereof (HEDTA), dihydroxy ethylethylenediamine diacetic acid and/or a salt thereof (DHEDTA), 1,3-propanediamine tetraacetic acid and/or a salt thereof (PDTA), diethylenetriamine pentaacetic acid and/or a salt thereof (DTPA), triethylenetetramine hexaacetic acid and/or a salt thereof (TTHA), nitrilotriacetic acid and/or a salt thereof (NTA), hydroxyethylimino diacetic acid and/or a salt thereof (HIMDA) and the like can be mentioned. Since a superior thickening effect is exhibited, those unneutralized are particularly preferable, such as ethylenediamine tetraacetic acid, disodium ethylenediaminetetraacetate, dihydroxy ethylethylenediamine diacetic acid, 1,3-propanediamine tetraacetic acid and diethylene triamine pentaacetic acid, and ethylenediamine tetraacetic acid and disodium ethylenediaminetetraacetate are particularly preferable.

As the chelating agent for component (F), one kind or two or more kinds may be used in combination. While its content is not particularly limited, it is preferably 0.01-1.0 wt %, more preferably 0.05-0.5 wt %, relative to the whole composition. When the content of component (E) is less than 0.01 wt %, a sufficient thickening effect cannot be obtained, and the chelating performance that should be afforded by the chelating agent is not sufficiently obtained.

The thickening composition of the present invention can appropriately contain, besides the aforementioned essential components, various optional components used for general cosmetic compositions, quasi drugs and the like, to the extent that the effect of the invention is not inhibited. Specifically, components including oil agents (camellia oil, corn oil, olive oil, rape oil, coconut oil, palm oil, hydrogenated castor oil, bee wax, liquid lanolin, liquid paraffin, squalene, vaseline, chain polysiloxane such as dimethylpolysiloxane and the like, cyclic polysiloxane such as octamethylcyclotetrasiloxane and the like, amino-modified silicone oil and the like), surfactants (ionic surfactants such as aklylsulfate, alkylether sulfate ester salt, fatty acid salt, sulfosuccinate, α-olefinsulfonate, N-acylsarcosinate, N-acylmethyltaurine salt, alkylethercarboxylate, phosphate ester salt and the like, imidazoline ampholytic surfactant, betaine ampholytic surfactant etc.), thickeners (polymer thickeners such as guar gum, starch, carageenan, xanthan gum, ethylcellulose, methylhydroxypropylstarch, carboxymethylcellulose, carboxyvinyl polymer, bentonite, hectorite, and the like), preservative, fragrance, UV absorber, moisturizing agent, physiologically active component, antioxidant, anti-inflammatory agent, antibacterial agent, antiperspirant, neutralizer, pH adjusting agent and the like can be mentioned, which can be added depending on the specific use and forms of the cleansing compositions and cosmetic compositions.

While the use of the thickening composition of the present invention is not particularly limited, various cleansing compositions and cosmetic compositions can be provided. For example, cosmetic soap, facial cleanser (cream•paste, liquid•gel, using aerosol and the like), cleansing cosmetics such as shampoo and the like, hair cosmetics such as hair treatment agents (including cream, mist, oil, gel, other forms and split-ends coating agent), hair setting agents (hair oil, setting lotion, curler lotion, pomade, stick pomade, pomade for Japanese hairdos, hair spray, hair mist, hair liquid, hair foam, hair gel, water grease) and the like, basic skin care such as general cream•skin milk (cleansing cream, cold cream, vanishing cream, hand cream and the like), shaving cream (after shaving cream, shaving cream and the like), lotion (hand lotion, general face lotion and the like), shaving lotion (after shaving lotion, shaving lotion and the like), cosmetic oil, pack and the like, make-up cosmetics such as foundation (cream, liquid and the like), eye cream•eye shadow mascara and the like, perfumes such as general perfume, cream perfume, powder perfume and the like, sunburn•sunburn proof cosmetics such as sunburn•sunburn proof cream, sunburn•sunburn proof lotion, sunburn•sunburn proof oil and the like, nail cosmetics such as nail cream•enamel•enamel remover and the like, eye liner cosmetics, lip cosmetics such as lip stick•lip cream and the like, mouth cavity cosmetics such as toothpaste and the like, bath cosmetics such as bath salt, bath oil and the like, and the like can be mentioned. Application to cleansing cosmetics, hair cosmetics and the like is preferable, since the sense of use is superior.

EXAMPLES

The present invention is explained in detail in the following by referring to Examples, which are not to be construed as limitative.

Example 1-Example 10

Thickening compositions and cleansing compositions having the formulations described in the following Table 1 were prepared, and evaluated for the viscosity thereof by the following method.
(Viscosity measurement) The viscosity at 25° C. was measured with a Brookfield viscometer (manufactured by TOKIMC, DVL-B) after using a rotor No. 3 or No. 4 at 30 rpm for 30 seconds.

TABLE 1

| | Ex. 1 | Ex. 2 | Ex. 3 | Comp. Ex. 1 | Comp. Ex. 2 | Comp. Ex. 3 |
|---|---|---|---|---|---|---|
| triethanolamine cocoyl glutamate (30% aqueous solution) | 67.0 | — | — | — | — | — |
| sodium cocoyl glutamate | — | 20.0 | 20.0 | 20.0 | 20.0 | — |
| glyceryl monolaurate | — | 6.0 | 8.0 | — | 8.0 | 8.0 |
| glyceryl monocaprate | 14.0 | — | — | — | — | — |
| calcium chloride | 0.2 | 1.6 | 1.6 | 1.6 | — | 1.6 |
| water | 18.8 | 72.4 | 70.4 | 78.4 | 72.0 | 90.4 |
| wt % | 100.0 | 100.0 | 100.0 | 100.0 | 100.0 | 100.0 |
| viscosity (mPa·s) | 700 | 3600 | 1800 | 30 | 50 | precipitation |

| | Ex. 4 | Ex. 5 | Ex. 6 | Ex. 7 | Comp. Ex. 4 | Comp. Ex. 5 | Comp. Ex. 6 | Comp. Ex. 7 |
|---|---|---|---|---|---|---|---|---|
| sodium cocoyl glutamate | 24.0 | 27.0 | 26.0 | 24.0 | 24.0 | 27.0 | 26.0 | 24.0 |
| butyleneglycol laurate | 6.0 | — | — | 8.0 | 6.0 | — | — | 8.0 |
| propyleneglycol laurate | — | 9.0 | — | — | — | 9.0 | — | — |
| propyleneglycol stearate | — | — | 7.8 | — | — | — | 7.8 | — |
| calcium chloride | 4.5 | 1.5 | 2.1 | — | — | — | — | — |
| magnesium chloride | — | — | — | 2.8 | — | — | — | — |
| water | 65.5 | 62.5 | 64.1 | 65.2 | 70.0 | 64.0 | 66.2 | 68.0 |
| | 100.0 | 100.0 | 100.0 | 100.0 | 100.0 | 100.0 | 100.0 | 100.0 |
| viscosity (mPa·s) | 930 | 4090 | 2060 | 2600 | 23 | 11 | 15 | 81 |

| | Ex. 8 | Ex. 9 | Ex. 10 | Comp. Ex. 8 | Comp. Ex. 9 | Comp. Ex. 10 |
|---|---|---|---|---|---|---|
| sodium cocoyl glutamate | 24.0 | 24.0 | 24.0 | 24.0 | 24.0 | 24.0 |
| diethyleneglycol laurate | — | — | — | — | — | — |
| cocoyl N-methylethanolamide | 8.0 | — | — | 8.0 | — | — |
| lauryl glycol hydroxypropyl ether | — | 5.0 | — | — | 5.0 | — |
| polyoxyethylene(1) coconut fatty acid monoisopropanolamide | — | — | 6.0 | — | — | 6.0 |
| magnesium chloride | 2.8 | 2.8 | 3.7 | — | — | — |
| water | 65.2 | 68.2 | 66.3 | 68.0 | 71.0 | 70.0 |
| | 100.0 | 100.0 | 100.0 | 100.0 | 100.0 | 100.0 |
| viscosity (mPa·s) | 3360 | 3780 | 1530 | 100 | 120 | 70 |

| | Comp. Ex. 11 | Comp. Ex. 12 | Comp. Ex. 13 | Comp. Ex. 14 |
|---|---|---|---|---|
| sodium cocoyl glutamate | 22.0 | 26.0 | 24.0 | 24.0 |
| triglycerol monolaurate | 8.2 | — | — | — |
| trioctanoin | — | 7.8 | — | — |
| PEG-10polyglyceryl-2 laurate | — | — | 5.0 | — |
| cetyl caprate | — | — | — | 8.0 |
| calcium chloride | 1.6 | 2.1 | 2.3 | 1.6 |
| water | 68.2 | 64.1 | 68.7 | 66.4 |
| | 100.0 | 100.0 | 100.0 | 100.0 |
| viscosity (mPa·s) | 52 | separation | separation | separation |

As is clear from the results of Table 1-1-4, to obtain the thickening composition of the present invention containing component (A) N-long-chain acyl acidic amino acid and/or a salt thereof, an amphipathic substance for component (B), an inorganic salt for component (C), and water for component (D) are essential components, where absence of any one of these components prevents provision of the thickening composition. It was further found that an amphipathic substance incapable of satisfying [formula 1] (inorganic value)≦−5× (organic value)+2500 failed to afford a thickening composition (Comparative Examples 11-14).

Example 11-Example 20

The thickening composition of the present invention was added to the cleansing compositions having formulations described in the following Table 2 at an optional ratio (Example 11-Example 20), and the viscosity was similarly measured.

TABLE 2

| | Ex. 11 | Ex. 12 | Ex. 13 | Comp. Ex. 15 | Comp. Ex. 16 | Comp. Ex. 17 | Comp. Ex. 18 |
|---|---|---|---|---|---|---|---|
| sodium laureth sulfate (27% aqueous solution) | 40.0 | 40.0 | 40.0 | 40.0 | 40.0 | 40.0 | 40.0 |

TABLE 2-continued

|  |  |  |  |  |  |  |  |
|---|---|---|---|---|---|---|---|
| cocamidopropyl betaine (30% aqueous solution) | 10.0 | 10.0 | 10.0 | 10.0 | 10.0 | 10.0 | 10.0 |
| PCA-Na (50% aqueous solution) | 2.0 | 2.0 | 2.0 | 2.0 | 2.0 | 2.0 | 2.0 |
| sodium chloride | 0.8 | 0.8 | 0.8 | 0.8 | 0.8 | 0.8 | 0.8 |
| polyquaternium-10 | 0.2 | 0.2 | 0.2 | 0.2 | 0.2 | 0.2 | 0.2 |
| water | 27.0 | 27.0 | 27.0 | 27.0 | 27.0 | 27.0 | 27.0 |
| sodium cocoyl glutamate | 1.2 | 2.4 | 4.8 | — | 1.2 | 2.4 | 4.8 |
| glyceryl monolaurate | 0.4 | 0.8 | 1.6 | — | — | — | — |
| calcium chloride | 0.1 | 0.2 | 0.3 | — | — | — | — |
| water | 18.3 | 16.6 | 13.3 | 20.0 | 18.8 | 17.6 | 15.2 |
|  | 100.0 | 100.0 | 100.0 | 100.0 | 100.0 | 100.0 | 100.0 |
| viscosity (mPa·s) | 460 | 540 | 1050 | 1110 | 170 | 40 | 30 |

|  | Comp. Ex. 19 | Comp. Ex. 20 | Comp. Ex. 21 |
|---|---|---|---|
| sodium laureth sulfate liquid (27% aqueous solution) | 40.0 | 40.0 | 40.0 |
| cocamidopropyl betaine (30% aqueous solution) | 10.0 | 10.0 | 10.0 |
| PCA-Na (50% aqueous solution) | 2.0 | 2.0 | 2.0 |
| sodium chloride | 0.8 | 0.8 | 0.8 |
| polyquaternium-10 | 0.2 | 0.2 | 0.2 |
| water | 27.0 | 27.0 | 27.0 |
| sodium cocoyl glutamate | 1.2 | 2.4 | 4.8 |
| glyceryl monolaurate | 0.4 | 0.8 | 1.6 |
| calcium chloride | — | — | — |
| water | 18.4 | 16.8 | 13.6 |
|  | 100.0 | 100.0 | 100.0 |
| viscosity (mPa·s) | 187 | 63 | 81 |

|  | Ex. 14 | Ex. 15 | Comp. Ex. 22 | Comp. Ex. 23 |
|---|---|---|---|---|
| sodium laureth sulfate (27% aqueous solution) | 35.0 | 35.0 | 35.0 | 35.0 |
| cocamidopropyl betaine (30% aqueous solution) | 15.0 | 15.0 | 15.0 | 15.0 |
| PCA-Na (50% aqueous solution) | 2.0 | 2.0 | 2.0 | 2.0 |
| PEG-7 glyceryl cocoate | 2.0 | 2.0 | 2.0 | 2.0 |
| behenyl alcohol | — | — | 2.5 | 2.5 |
| polyquaternium-10 | 0.2 | 0.2 | 0.2 | 0.2 |
| water | 25.8 | 25.8 | 23.3 | 23.3 |
| sodium cocoyl glutamate | 1.5 | — | — | 1.5 |
| sodium stearoyl glutamate | — | 1.5 | 1.5 | — |
| glyceryl monolaurate | 2.5 | 2.5 | — | — |
| magnesium chloride 6-hydrate | 0.6 | 0.1 | — | — |
| water | 15.4 | 15.9 | 18.5 | 18.5 |
|  | 100.0 | 100.0 | 100.0 | 100.0 |
| viscosity (mPa·s) | 17400 | 37100 | separation | 117 |

|  | Ex. 16 | Ex. 17 | Ex. 18 | Ex. 19 | Ex. 20 |
|---|---|---|---|---|---|
| sodium laureth sulfate (27% aqueous solution) | 35.0 | 35.0 | 35.0 | 35.0 | 35.0 |
| cocamidopropyl betaine (30% aqueous solution) | 15.0 | 15.0 | 15.0 | 15.0 | 15.0 |
| PCA-Na (50% aqueous solution) | 2.0 | 2.0 | 2.0 | 2.0 | 2.0 |
| PEG-7 glyceryl cocoate | 2.0 | 2.0 | 2.0 | 2.0 | 2.0 |
| polyquaternium-10 | 0.2 | 0.2 | 0.2 | 0.2 | 0.2 |
| triethanolamine cocoyl glutamate (30% aqueous solution) | 16.6 | 16.6 | 16.6 | 16.6 | 16.6 |
| glyceryl monolaurate | 2.0 | 2.0 | 2.0 | 2.0 | 2.0 |
| magnesium chloride 6-hydrate | 0.2 | 0.2 | 0.2 | 0.2 | 0.2 |
| glycerol | — | 5.0 | — | — | — |
| diglycerol | — | — | 5.0 | — | — |
| sorbitol (70% aqueous solution) | — | — | — | 7.1 | — |
| disodium ethylenediaminetetraacetate | — | — | — | — | 0.2 |
| water | 27.0 | 22.0 | 22.0 | 19.9 | 26.8 |
|  | 100.0 | 100.0 | 100.0 | 100.0 | 100.0 |
| viscosity (mPa·s) | 3709 | 4680 | 4820 | 8130 | 5600 |

As is clear from the results of Table 2, when addition of component (A), sodium cocoyl glutamate, to a skin or hair cleansing composition (Comparative Example 15) containing polyoxyethylene alkylether sulfate (laureth sulfate) as a main component was attempted, the viscosity markedly decreased as the amount of the addition increased (Comparative Example 16-Comparative Example 18). Moreover, when component (A), sodium cocoyl glutamate, and component (B), glyceryl monolaurate, were added to a skin or hair cleansing composition containing polyoxyethylene alkylether sulfate (laureth sulfate) as a main component (Comparative Example 15), sufficient viscosity as a cleansing composition could not be obtained (Comparative Example 19-Comparative Example 23). In contrast, when the thickening composition of the present invention was added, a cleansing composition containing N-acyl acidic amino acid and/or a salt thereof and having a suitable viscosity was obtained (Example 11-Example 13). Moreover, the thickening effect could be increased by adding polyhydric alcohol and/or chelating agents to a cleansing composition (Example 16) containing the thickening composition of the present invention (Example 17-Example 20). From the foregoing, higher contents of the thickening composition of the present invention afforded higher viscosity, and a technique for adding greater amounts of N-acyl acidic amino acid and/or a salt thereof, which has been unattainable by conventional techniques, has been achieved by the present invention.

Formulation Examples 1-3

Liquid cleansing compositions of the following formulations were prepared according to conventional methods. As a result, good viscosity and superior sense of use could be afforded.

Formulation Example 1

| shampoo composition | |
|---|---|
| | (wt %) |
| sodium laureth sulfate (27% aqueous solution) | 35.0 |
| cocamidopropyl betaine (30% aqueous solution) | 15.0 |
| PCA-Na (50% aqueous solution) | 2.0 |
| PEG-7 glyceryl cocoate | 2.0 |
| polyquaternium-10 | 0.2 |
| cocamide MEA | 0.2 |
| citric acid | q.s. |
| dimethicone | 0.3 |
| ceteareth-60 myristyl glycol | 0.4 |
| preservative | q.s. |
| TEA cocoyl glutamate (30% aqueous solution) | 20.0 |
| glyceryl laurate | 1.8 |
| magnesium chloride (6-hydrate) | 0.2 |
| glycerol | 3.0 |
| disodium EDTA | 0.2 |
| water | residual amount |
| total | 100.0 |

Formulation Example 2

| shampoo composition | |
|---|---|
| | (wt %) |
| sodium laureth sulfate (27% aqueous solution) | 30.0 |
| cocamidopropyl betaine (30% aqueous solution) | 15.0 |
| PCA-Na (50% aqueous solution) | 2.0 |
| PEG-7 glyceryl cocoate | 2.0 |
| polyquaternium-10 | 0.2 |
| cocoamide DEA | 0.2 |
| citric acid | q.s. |
| dimethicone | 0.3 |
| ceteareth-60 myristyl glycol | 0.4 |
| glycol distearate | 1.0 |
| preservative | q.s. |
| TEA cocoyl glutamate (30% aqueous solution) | 25.0 |
| glyceryl laurate | 2.6 |
| magnesium chloride (6-hydrate) | 0.3 |
| sorbitol (70% aqueous solution) | 6.0 |
| disodium EDTA | 0.2 |
| water | residual amount |
| total | 100.0 |

Formulation Example 3

| shower gel composition | |
|---|---|
| | (wt %) |
| sodium laureth sulfate (27% aqueous solution) | 35.0 |
| cocamidopropyl betaine (30% aqueous solution) | 15.0 |
| PCA-Na (50% aqueous solution) | 2.0 |
| PEG-7 glyceryl cocoate | 2.0 |
| polyquaternium-10 | 0.2 |
| cocoamide DEA | 0.2 |
| citric acid | q.s. |
| dimethicone | 0.3 |
| phytosteryl/octyldodecyl lauroyl glutamate | 0.2 |
| glycol distearate | 1.0 |
| preservative | q.s. |
| sodium cocoyl glutamate | 5.0 |
| butyleneglycol laurate | 2.0 |
| magnesium chloride (6-hydrate) | 0.2 |
| sorbitol (70% aqueous solution) | 6.0 |
| disodium EDTA | 0.2 |
| water | residual amount |
| total | 100.0 |

INDUSTRIAL APPLICABILITY

By adding an amphipathic substance, an inorganic salt and water at particular ratios to N-long-chain acyl acidic amino acid and/or a salt thereof well known as a material difficult to be thickened, suitable thickening performance and superior usability can be afforded. Addition of the thickening composition has enabled provision of cleansing compositions and cosmetic compositions for skin, hair and the like, which maintain thickening performance and usability, while containing N-long-chain acyl acidic amino acid and/or a salt thereof.

This application is based on patent application Nos. 2004-37365 and 2004-271394 filed in Japan, the contents of which are incorporated in full herein by this reference.

The invention claimed is:

1. A thickening composition, comprising:
(A) at least one N-long-chain acyl glutamic acid and/or a salt thereof;
(B) at least one amphipathic substance having an organic value and an inorganic value satisfying formula (1):

$$(\text{inorganic value}) \leq -5 \times (\text{organic value}) + 2500 \qquad (1);$$

(C) at least one inorganic salt; and
(D) water,
wherein
the N-long-chain acyl glutamic acid and/or a salt thereof is the sole N-long-chain acyl amino acid and/or a salt thereof in the composition, the thickening composition has a viscosity of not less than 200 mPa·s, the weight ratio of (A) to (C) is 99:1 to 55:45, and the weight ratio to the total combined amount of (A), (B) and (C) to (D) ((A+B+C)/D) is 2.5:97.5 to 50:50.

2. The thickening composition of claim 1, wherein (B) comprises at least one member selected from the group consisting of glyceryl monofatty acid, propyleneglycol monofatty acid, butyleneglycol monofatty acid, diethyleneglycol monofatty acid, monofatty acid N-methylethanolamide, lauryl glycol hydroxypropylether, and polyoxypropylene(1)coconut fatty acid monoisopropanolamide.

3. The thickening composition of claim 1, wherein the weight ratio of (A):(B) is 90:10 to 30:70 and the weight ratio of the total weight of (A), (B), and (C):(D) is 2:98 to 70:30.

4. The thickening composition claim 2, wherein the weight ratio of (A):(B) is 90:10 to 30:70 and the weight ratio of the total weight of (A), (B), and (C):(D) is 2:98 to 70:30.

5. The thickening composition of claim 1, wherein the acyl group of (A) derives from one or more members selected from the group consisting of caprylic acid, capric acid, lauric acid, myristic acid, stearic acid, palmitic acid, oleic acid, linoleic acid, behenic acid, coconut fatty acid, palm fatty acid, hydrogenated beef tallow fatty acid, and mixtures thereof.

6. The thickening composition of claim 2, wherein the acyl group of (A) derives from one or more members selected from the group consisting of caprylic acid, capric acid, lauric acid, myristic acid, stearic acid, palmitic acid, oleic acid, linoleic acid, behenic acid, coconut fatty acid, palm fatty acid, hydrogenated beef tallow fatty acid, and mixtures thereof.

7. The thickening composition of claim 1, wherein (B) comprises a glycerylmonofatty acid having not less than 8 and not more than 18 carbon atoms.

8. The thickening composition of claim 2, wherein (B) comprises a glyceryl monofatty acid having not less than 8 and not more than 18 carbon atoms.

9. The thickening composition of claim 1, wherein (C) comprises an alkali metal inorganic salt.

10. The thickening composition of claim 1, wherein (C) comprises an alkaline earth metal inorganic salt.

11. The thickening composition claim 1, further comprising:
(E) at least one polyhydric alcohol.

12. The thickening composition of claim 1, further comprising:
(F) at least one chelating agent.

13. The thickening composition of claim 1, wherein (B) comprises at least one member selected from the group consisting of propyleneglycol monofatty acid, butyleneglycol monofatty acid, diethyleneglycol monofatty acid, monofatty acid N-methylethanolamide, lauryl glycol hydroxypropylether, and polyoxypropylene(1)coconut fatty acid monoisopropanolamide.

14. The thickening composition of claim 1, wherein (C) is selected from the group consisting of sodium chloride, potassium chloride, magnesium chloride, calcium chloride, sodium sulfate, sodium hydrogensulfate, potassium sulfate, potassium hydrogensulfate, magnesium sulfate, calcium sulfate, monobasic sodium phosphate, dibasic sodium phosphate, monobasic potassium phosphate, dibasic potassium phosphate, sodium carbonate, sodium hydrogencarbonate, potassium carbonate, potassium hydrogencarbonate, magnesium carbonate, calcium carbonate and mixtures thereof.

15. The thickening composition of claim 1, wherein (C) comprises a calcium salt.

16. The thickening composition of claim 1, wherein (C) comprises a magnesium salt.

17. The thickening composition of claim 1, wherein the acyl component of (A) is derived from a straight chain or branched chain acyl group derived from saturated or unsaturated fatty acids having 8 to 22 carbon atoms.

18. The thickening composition of claim 1, wherein the acyl component of (A) is derived from coconut fatty acid, lauric acid or myristic acid.

19. The thickening composition of claim 1, which consists essentially of (A), (B), (C) and (D).

20. The thickening composition of claim 1, which consists of (A), (B), (C) and (D).

21. The thickening composition of claim 1, wherein (B) comprises at least one member selected from the group consisting of glyceryl monocaprylate, glyceryl monocaprate, glyceryl monolaurate, glyceryl monomyristate, glyceryl monopalmitate, glyceryl monostearate, glyceryl monoisostearate, propyleneglycol monocaprylate, propyleneglycol monocaprate, propyleneglycol monolaurate, propyleneglycol monomyristate, propyleneglycol monopalmitate, propyleneglycol monostearate, propyleneglycol monoisostearate, butyleneglycol monocaprylate, butyleneglycol monocaprate, butyleneglycol monolaurate, butyleneglycol monomyristate, butyleneglycol monopalmitate, butyleneglycol monostearate, butyleneglycol monoisostearate, diethyleneglycol monocaprylate, diethyleneglycol monocaprate, diethyleneglycol monolaurate, diethyleneglycol monomyristate, diethyleneglycol monopalmitate, diethyleneglycol monostearate, diethyleneglycol monoisostearate, monocapryloyl N-methylethanolamide, monocaproyl N-methylethanolamide, monolauroyl N-methylethanolamide, monomyristoyl N-methylethanolamide, monopalmitoyl N-methylethanolamide, monostearoyl N-methylethanolamide and monoisostearoyl N-methylethanolamide.

22. The thickening composition of claim 1, which contains 0.2-60% by weight of (A).

23. The thickening composition of claim 1, which contains 3-35% by weight of (A).

24. The thickening composition of claim 1, which has a viscosity of 200 mPa·s to 50,000 mPa·s.

25. The thickening composition of claim 1, which has a viscosity of 250 mPa·s to 40,000 mPa·s.

26. The thickening composition of claim 1, which has a viscosity of 300 mPa·s to 25,000 mPa·s.

27. The thickening composition of claim 1, which has a viscosity of 350 mPa·s to 10,000 mPa·s.

28. A cleansing composition, comprising a thickening composition of claim 1.

29. A cosmetic composition, comprising a thickening composition of claim 1.

30. A method of making the thickening composition of claim 1, comprising combining (A), (B), (C) and (D).

* * * * *